(12) United States Patent
Zimmermann et al.

(10) Patent No.: US 7,417,224 B2
(45) Date of Patent: Aug. 26, 2008

(54) ION MOBILITY SPECTROMETER WITH PARALLEL DRIFT GAS AND ION CARRIER GAS FLOWS

(75) Inventors: Stefan Zimmermann, Lübeck (DE); Wolfgang Bäther, Lübeck (DE)

(73) Assignee: Dräger Saftey AG & Co. KGaA, Lübeck (DE)

( * ) Notice: Subject to any disclaimer, the term of this patent is extended or adjusted under 35 U.S.C. 154(b) by 185 days.

(21) Appl. No.: 11/420,116

(22) Filed: May 24, 2006

(65) Prior Publication Data
US 2007/0023647 A1    Feb. 1, 2007

(30) Foreign Application Priority Data
Jul. 2, 2005    (DE) .................. 10 2005 031 048

(51) Int. Cl.
*H01J 49/40* (2006.01)
(52) U.S. Cl. ....................... 250/286; 250/287
(58) Field of Classification Search ................. 250/286, 250/287, 281, 282
See application file for complete search history.

(56) References Cited

U.S. PATENT DOCUMENTS

| | | | |
|---|---|---|---|
| 3,835,328 A | 9/1974 | Harris et al. | |
| 3,870,888 A | 3/1975 | Lovelock | |
| 4,075,550 A | 2/1978 | Castleman et al. | |
| 4,777,363 A | 10/1988 | Eiceman et al. | |
| 5,047,723 A | 9/1991 | Puumalainen | |
| 5,223,712 A | 6/1993 | Adams et al. | |
| 5,455,417 A * | 10/1995 | Sacristan | 250/287 |
| 6,495,823 B1 | 12/2002 | Miller et al. | |
| 6,630,663 B2 * | 10/2003 | Murphy et al. | 250/286 |
| 7,244,931 B2 * | 7/2007 | Zimmermann et al. | 250/292 |

(Continued)

FOREIGN PATENT DOCUMENTS

WO    WO9416320    7/1994

OTHER PUBLICATIONS

Spangler et al., Membrane Inlet for Ion Mobility Spectrometry (Plasma Chromatography), Journal, Mar. 21, 1983, 267-287, International Journal of Mass Spectrometry and Ion Physics, 52 (1983) 267-287 Elsevier Science Publishers B.V., Amsterdam—Printed in the Netherlands.

*Primary Examiner*—Kiet T Nguyen
(74) *Attorney, Agent, or Firm*—McGlew & Tuttle, P.C.

(57) ABSTRACT

An ion mobility spectrometer is provided with at least one ionization chamber (1) through which analyte-containing gas can flow. A radiation source (2) is provided from which ionizing radiation is suitable for ionizing the analyte-containing gas at least partially, enters the ionization space (1). A separation area is located behind the ionization space (1) in the direction of flow, into which the partially ionized gas is admitted as an ion carrier gas (4) and a nearly ion-free gas is admitted as a drift gas (5) in such a way that a flow in which predominantly ion carrier gas (4) flows through cross-sectional areas (6) and predominantly drift gas (5) flows through other cross-sectional areas (7, 7'), becomes established at least in the inlet area of the separation area (8). The drift gas (5) and ion carrier gas (4) flow unidirectionally and the cross-sectional areas (6), through which predominantly ion carrier gas (4) flows, are smaller in at least one dimension than the cross-sectional areas (7, 7'), through which predominantly drift gas (5) flows.

51 Claims, 16 Drawing Sheets

U.S. PATENT DOCUMENTS

2003/0155505 A1    8/2003  Murphy et al.
2006/0054804 A1*   3/2006  Wexler .................. 250/282
2006/0192097 A1*   8/2006  Anttalainen ............. 250/281

* cited by examiner

ION MOBILITY SPECTROMETER WITH PARALLEL DRIFT GAS AND ION CARRIER GAS FLOWS

CROSS REFERENCE TO RELATED APPLICATIONS

This application claims the benefit of priority under 35 U.S.C. § 119 of German Patent Application DE 10 2005 031 048.6 filed Jul. 2, 2005, the entire contents of which are incorporated herein by reference.

FIELD OF THE INVENTION

The present invention pertains to an ion mobility spectrometer with parallel drift gas and ion carrier gas flows.

BACKGROUND OF THE INVENTION

Ion mobility spectrometers (IMS) are used to detect trace substances in the air. They are widely used especially for detecting explosives, illegal drugs, chemical warfare agents and toxic industrial gases. The characteristic assembly units of an ion mobility spectrometer are the ionization chamber, the drift chamber and detectors. The ionization chamber and the drift chamber are usually separated by a grid in conventional ion mobility spectrometers. The analyte molecules to be determined are converted into ions in the ionization chamber. The ions formed are transferred from the ionization chamber into the drift chamber as an ion swarm by the action of an electric field. The analyte ions fly through the drift chamber against the resistance of the drift gas under the effect of a high-voltage electric field and are detected by the detector, due to the differences in the mobilities of different ions, in a time-resolved manner, since different analyte ions show different interactions with the drift gas, and therefore they also have different flight times and can thus be separated from one another.

Ion mobility spectrometers in which the drift gas flows from the detector in the direction of the ionization chamber have been known. The analyte gas is ionized and flows in the direction of the grid within the ionization chamber. The ions formed are consequently moving with the analyte gas in the direction of the grid against the direction of flow of the drift gas and then to the detector under the effect of a high-voltage field (Spangler and Carrico, *Int. J. Mass Spectrom. Ion Phys.*, 1983, 52, 627).

Unidirectional flow guiding is described by Eiceman in U.S. Pat. No. 4,777,363, in which the analyte gas is introduced into the device on the detector side and leaves the device on the ionization chamber side. The ionization takes place in the ionization chamber and ions are accelerated toward the detector against the analyte gas flow. The drift gas and the analyte gas are identical here.

Both systems require a uniform electric field within the drift chamber for the separation of the ions. This field is built up by a series of ring electrodes, which are all electrically insulated. The necessary high voltage is usually 2,000-3,000 V. Such systems are very expensive, complicated to manufacture and can only be miniaturized with difficulty.

Contrary to the above-described IMS, it is, furthermore, known that the ions to be separated can be guided unidirectionally with the drift gas flow. The ions can be deflected from this direction of flow by a relatively low voltage. If they then reach electrodes, which are formed by the walls, they can be discharged, and a current can be measured. The drift gas and the analyte gas are identical here.

Such a system is found in so-called electron capture detectors. An early example is disclosed by Lovelock in U.S. Pat. No. 3,870,888. Total ionic currents can be measured with such systems. By contrast, it is not possible to distinguish different ion species.

It is known that long-lived ions can be separated from short-lived ones by extending the drift paths, e.g., by installing baffles. This principle is described, for example in connection with the detection of chemical warfare agents (U.S. Pat. Nos. 3,835,328, 4,075,550 as well as 5,223,712). The separation efficiency of such systems is relatively low, which may lead relatively frequently to the triggering of a false alarm.

An improvement is described in U.S. Pat. No. 5,047,723 by Puumalainen. The gas flow to be analyzed is first ionized here and then passed through a series of electric deflecting fields. Depending on the type of the ions, the ions are discharged at different electrodes. The current is measured and is an indicator of analytes that are present.

In WO 9416320, Paakanen et al. modified such a system once again and identified substances on the basis of their characteristic patterns, which are obtained from a plurality of electrodes connected in series at closely spaced locations from one another due to ion discharge. Besides ion signals, signals of semiconductor sensors are also included in a pattern recognition.

Furthermore, it is known that the last-named system can be improved by heating the analyte gas before the analysis and by the sensor electrodes forming multidimensional arrays (US 2003/0155503 A1). The signal evaluation is based on pattern recognition in this case as well. The drawback that the measuring system must first learn the particular pattern, i.e., that an extremely great calibrating effort is necessary, is associated with this. This applies especially to mixtures. Mixtures that are not taken into account, i.e., for example, combinations of analytes to be monitored with unknown impurities, may lead to false alarms or hinder the detection of the analytes to be monitored.

Finally, it is known that the analyte ions can be deflected by a high-frequency alternating field, to which a low compensation voltage is superimposed. The analyte ions are likewise transported here in a system in the direction of the drift gas (U.S. Pat. No. 6,495,823). A defined analyte ion species is let through the system and reaches the detector under defined conditions of the alternating field and the compensation voltage only. These ion sensors, which can be manufactured in a compact form, can be combined in arrays. However, such systems are expensive and extremely susceptible to ambient effects, such as pressure and moisture.

SUMMARY OF THE INVENTION

The object of the present invention is to propose an ion mobility spectrometer that can be manufactured at low cost, is insensitive to variations in the ambient conditions, especially the ambient moisture, has good separation efficiency at high reliability of recognition and which is suitable for miniaturization based on its principle of operation.

The present invention is based on a concentration of analyte ions to be detected in a defined cross-sectional area of the inlet zone of a separation area, through which flow takes place. This is achieved by the introduction according to the present invention of an ion-containing ion carrier gas and of a nearly ion-free drift gas. The introduction takes place such that ion carrier gas and drift gas are moving through the separation area in the form of a preferably laminar flow in parallel next to one another, without becoming mixed to an appreciable extent. Due to the slight mixing of the flowing gases, the desired concentration of the analyte ions to be detected remains preserved in a defined cross-sectional area until the ions are exposed to the effect of an electric deflecting field.

The ions are deflected in the separation area at right angles to the direction of flow. Since the ions are fed into the separation area in a defined cross-sectional area only, all the ions that have equal mobility are imaged onto a marginal area of the separation area, whose location depends on the flow conditions in the separation area, the strength of the deflecting field, the mobility of the ions and the size and the location of the cross-sectional area in which the ions are fed into the separation area. Ions with a different mobility are deflected onto another marginal area. Due to the arrangement of a relatively small detector electrode on the marginal area of the separation area, it is possible to measure the current that is caused by ions of a defined mobility. This current is an indicator of the concentration of the ions of precisely this defined mobility. The feed of the analyte ions according to the present invention and the maintenance of the flow conditions lead to the analyte ions being focused on a defined cross-sectional area, from which the ions are extracted by the deflecting field. The effectiveness of focusing the analyte ions to a defined cross-sectional area is substantially increased when the velocity of flow of the drift gas is higher in the area in which the two gas flows meet than the velocity of flow of the ion carrier gas. The focusing of the ions makes other measures for concentrating analyte ions unnecessary. The focusing according to the present invention is at the same time the prerequisite for the evaluable segregation of analyte ions with different mobilities by an electric deflecting field at right angles to the direction of flow.

The designations ion carrier gas and drift gas will be maintained below to characterize the flow conditions, even though a carrier gas that has been completely freed from ions is possibly flowing in the separation area due to the action of the deflecting field and the ions are deflected through the drift gas, so that individual volume areas of the drift gas appear to be enriched with ions to an appreciable extent in the separation area.

The present invention is embodied by an ion mobility spectrometer, which comprises at least one ionization space, through which analyte-containing gas can flow, and at least one radiation source. Ionizing radiation, which is suitable for ionizing the analyte-containing gas at least partially, enters the ionization space from the radiation source. The analyte gas, which is at least partially ionized in the ionization space, is called ion carrier gas after it has left the ionization space.

At least one separation area, in which predominantly ion carrier gas flows through cross-sectional areas and predominantly drift gas flows through other cross-sectional areas, is located behind the ionization space in the direction of flow.

It may be advantageous to form, between the ionization space and the separation area, a separate transition area, into which at least partially ionized gas can be introduced as an ion carrier gas and a nearly ion-free gas can be introduced as a drift gas in such a way that a flow, in which predominantly ion carrier gas flows through cross-sectional areas and predominantly drift gas flows through other cross-sectional areas, becomes established at least at the end of the transition area. It is essential for the present invention that these flow conditions develop in the inlet area of the separation area.

If the plural is used below, the sum of the cross-sectional areas through which the same gas species flows is always meant for characterizing the relations of the cross-sectional areas.

The drift gas and the ion carrier gas flow unidirectionally and are fed in via separate gas inlets. The cross-sectional areas through which predominantly ion carrier gas flows are smaller in at least one dimension than the cross-sectional areas through which predominantly drift gas flows. The cross-sectional areas through which predominantly ion carrier gas flows are smaller at least in the dimension of the electric field component that is at right angles to the direction of flow than the cross-sectional areas through which predominantly drift gas flows. As a result, focusing of the analyte ions takes place according to the present invention in defined cross-sectional areas. This focusing takes place especially effectively if the drift gas is flowing at a higher velocity in the merging area than the ion carrier gas. An advantageous contraction of the flowing ion carrier gases takes place in this case.

At least one detector electrode, at least one auxiliary electrode and at least one counterelectrode are located in the separation area. These are arranged such that an electric field, which has at least one field component that is not parallel to the direction of flow in the separation area, can be formed between them. To make it possible to utilize the effect of focusing, it is important that at least one cross-sectional area, through which predominantly drift gas flows, is located between the cross-sectional areas through which predominantly ion carrier gas flows and the detector electrode.

Unlike in most of the prior-art IMS already described, the ions to be separated are guided unidirectionally with the drift gas flow. The ions are deflected from this direction of flow by a relatively low voltage. If they then reach the electrodes, which are preferably arranged in the vicinity of the separation area, they can be discharged, and a current can be measured.

This principle according to the present invention requires only relatively low deflecting voltages. As a result, the effort needed for the driving and evaluating electronic system decreases. Miniaturization can likewise be carried out more easily.

Reduced material consumption and lower costs will thus lead to further advantages of such arrangements. The design permits the continuous detection of the ions and thus a better detection limit.

Good mobility-dependent segregation of the analyte ions and hence improved separation efficiency of the IMS according to the present invention, even in miniaturized embodiments, are obtained already when the cross-sectional areas through which predominantly ion carrier gas flows have a dimension, at least in the direction of the electric field, that is smaller by a factor of at least 10 than the cross-sectional areas through which predominantly drift gas flows. The velocity of flow of the two gas flows must be at least equal. An especially effective mobility-dependent segregation of the analyte ions and hence improved separation efficiency of the IMS according to the present invention are obtained if the drift gas flows in at a higher velocity of flow than the ion carrier gas. Marked improvement of the separation efficiency is obtained already if the velocity of flow of the drift gas is 1.5 times higher.

Furthermore, it is advantageous for the operation of an IMS according to the present invention if at least one assembly unit is contained that is suitable for maintaining a drift gas circuit. As a result, the IMS becomes extensively independent from ambient conditions, especially variations in the ambient moisture. The effect of moisture becomes noticeable in this case only via differently conditioned ion carrier gases, whose volume percentage can be kept low compared to the volume percentage of the drift gas. It is especially advantageous if the drift gas circuit contains a filter for reducing the moisture and/or for removing analytes and/or ions from the drift gas.

The closed-circuit operation makes possible the highly economical operation of the filter, because the introduction of smaller amount of substances that are to be filtered out is associated with long service life of the filters.

The principle of operation of IMS according to the present invention is determined essentially by the radiation source used. It was found that it is advantageous if a radiation source is used that can convert the analyte-containing air introduced into the ionization chamber into ion carrier gas by the ionization of the air molecules in the ionization space, as a result of which subsequent ionization is made possible for the formation of analyte ions. Electron sources are especially suitable for this. Especially compact and simple designs can be embodied with beta radiators. Other electron sources or UV sources are suitable as well.

The analyte ions are focused according to the present invention by the focusing of the ion carrier gas. This can be affected even by a corresponding geometric design of the ionization space. However, it is advantageous if flow-carrying means are present, which lead to focusing of the ion carrier gas and bring about the development of a laminar flow of drift gas and ion carrier gas in the separation area. It is especially advantageous, furthermore, if the drift gas merges with the ion carrier gas at a higher velocity of flow than the velocity of flow of the ion carrier gas. As a result, the ion carrier gas is contracted. The efficiency of the focusing of the analyte ions according to the present invention increases substantially as a result in defined cross-sectional areas.

The ion yield, which is relevant for the sensitivity of an IMS according to the present invention, can be advantageously increased at least by surfaces that come into contact with the ion carrier gas being made of a material with a low surface energy. Teflon (Polytetrafluoroethylene—PTFE) has proved to be useful as such a material on several occasions.

Another factor that substantially affects the performance capacity of the IMS is to affect the shape of the electric deflecting field, mainly by the geometry of the electrodes and the potential distribution. It is advantageous if a circuit is contained that maintains the auxiliary electrodes and the detector electrode at the same electric potential. Furthermore, it proved to be advantageous if a circuit is contained that brings about a potential distribution at which the potential of the counterelectrode is either higher or lower than the potential of the detector electrode and that of the auxiliary electrodes. Thus, only ions of equal polarity are detected. Evaluation methods that lead to an especially high selectivity can be used if a circuit is contained that brings about a potential distribution at which the potential of the counterelectrode becomes alternatingly higher and lower than the potential of the detector electrode and the potential of the auxiliary electrodes. Moreover, the low deflecting voltages used according to the present invention make possible a rapid changeover of polarity.

Another advantage of the present invention is the possibility of spectral analysis by varying the deflecting voltage. Compared to usual pattern recognition methods, the effort needed to set up a pattern data bank is eliminated. To carry out a spectral analysis, it is advantageous if a circuit is present that carries out a potential distribution at which the potential difference between the counterelectrode and at least the detector electrode varies. A complete spectrum is obtained if the potential difference is continuously varied. Sections from an ion spectrum can be obtained, furthermore, in an advantageous manner if a potential distribution is created in which the potential difference between the counterelectrode and at least the detector electrode jumps between a plurality of fixed values. This embodiment is especially advantageous if the presence of selected substances is to be monitored.

It is advantageous for a detector electrode that acts selectively as a function of the potential applied if at least one auxiliary electrode is located in front of the detector electrode when viewed in the direction of flow. Especially uniform development of the electric deflecting field can be achieved if at least one auxiliary electrode is additionally located behind the detector electrode when viewed in the direction of flow.

It is possible to work with especially low deflecting voltages if the electrodes are arranged such that the electric field develops at right angles to the direction of flow. To embody the principle according to the present invention, it is sufficient, in principle, if the detector electrode consists of a single electrode. However, it is especially advantageous if the detector electrode consists of a plurality of sectors that can be wired individually. Individual sectors can thus be assigned in terms of connection to the detector electrode or an auxiliary electrode. As a result, the area of the detector electrode can be varied and the resolution, on the one hand, and the sensitivity of the IMS, on the other hand, can be affected depending on the requirements.

It is advantageous for optimal field geometry if all electrodes are arranged in parallel to one another, especially if the detector electrode and the auxiliary electrodes are located in one plane. It is likewise advantageous for the geometry of the field if the counterelectrodes are arranged in one area and the auxiliary electrodes are arranged in another area, and the surface areas of the areas are approximately of the same size, and designs in which these areas are located congruently opposite each other are to be preferred.

Especially well reproducible results are obtained if the electrodes consist of platinum or gold.

It is advantageous for the good separation efficiency of the IMS according to the present invention if the detector electrode is narrower at right angles to the direction of flow than the width of the cross-sectional areas in the separation area, through which predominantly ion carrier gas flows. Distortions of the spectrum due to ions from areas near the margin are thus avoided.

In addition to the variable geometry of the detector electrode, the dynamic range of the IMS can be expanded by working with a variable ion carrier gas flow. The effects of the change in the velocity of flow that are associated herewith can be compensated by calculation without problems.

The present invention will be explained in greater detail on the basis of exemplary embodiments. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
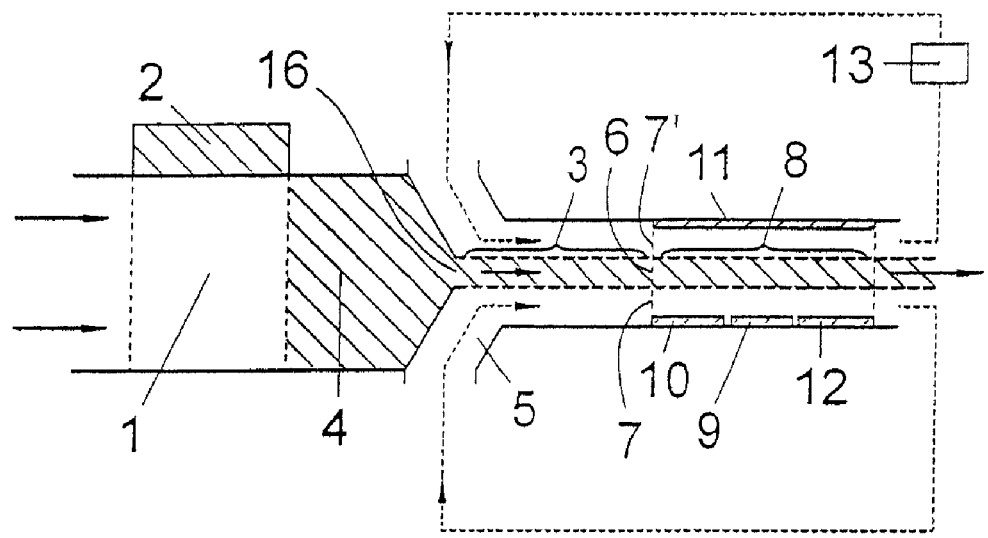
FIG. 1 is a schematic view of an ion mobility spectrometer according to the present invention.

Referring to the drawings in particular, FIG. 1 shows in a schematic view, an ion mobility spectrometer according to the present invention. This ion mobility spectrometer requires only a relatively low voltage, which is on the order of magnitude of below 50 V, for separating the ions and can therefore be manufactured at low cost. The gas flows that occur are indicated by arrows.

The IMS comprises an ionization space 1, a radiation source 2, which emits beta radiation, and a transition area 3. Analyte-containing gas flowing through the ionization space is partially ionized under the effect of the beta radiation. As a result, ion carrier gas is formed in the sense of the present invention, which flows into the transition area 3. Furthermore, a nearly ion-free drift gas 5 is introduced into the transition area 3. Ion carrier gas 4 and drift gas 5 are introduced into the transition area 3 in such a manner that a flow becomes established at least at the end of the transition area 3, in which predominantly ion carrier gas 4 flows through cross-sectional areas 6 and predominantly drift gas 5 flows through other cross-sectional areas 7, 7'. A separation area 8, in which the ions are exposed to the deflecting action of an electric field, which is built up between at least one detector electrode 9 with an auxiliary electrode 10 arranged in front of it and a counterelectrode 11, is located behind the transition area 3 in the direction of flow. Another auxiliary electrode 12, which ensures the especially uniform distribution of the electric field, is arranged behind the detector electrode in the direction of flow in this example. The nearly ion-free drift gas is drawn off after passing through the separation area 8, sent through a filter 13 and re-introduced into the transition area. The separation efficiency that can be attained with such an IMS is determined essentially by the focusing of the analyte ions in a defined cross-sectional area of the flowing gas. Flow-carrying means, which are designed in this case in the form of a diaphragm 16 with a slot-like opening, are used for this focusing. The ion carrier gas 4 now flows through the slot-like opening, i.e., mechanical contraction and focusing of the ion carrier gas take place. The ion carrier gas 4 merges laminarly with the drift gas 5 in the transition area behind the contraction. The contraction of the ion carrier gas 4 is further intensified if the drift gas 5 is introduced at a higher velocity of flow than the ion carrier gas 4.

Monitoring of the ambient air is a typical application of the invention being described here. The air to be analyzed flows into the ionization space 1, where the substances to be analyzed (analytes) contained in the air are ionized. The ionization by β-radiation (electrons) takes place in two steps. Predominantly nitrogen molecules are at first ionized by bombardment with high-energy electrons.

The analytes contained in the air are hardly ionized by the electron bombardment.

Stable $H^+(H_2O)_n$ and $O_2^-(H_2O)_n$ reactant ions as well as positive and negative analyte ion clusters are formed in subsequent reactions (G. Eiceman and Z. Karpas, *Ion mobility spectrometry*, 1994). After crossing the ionization space, the air contains ions and is called ion carrier gas.

A laminar flow, in which the ion carrier gas 4 is surrounded by drift gas 5 on two sides, develops in the transition area 3, which has a rectangular cross section in this example. The laminar flow is preserved in the separation area 8 because of the laminar flow conditions, so that the ions in the ion carrier gas enter the separation area 8 in a focused form. If the drift gas merges with the ion carrier gas at a higher velocity of flow compared to the velocity of flow of the ion carrier gas, the ion carrier gas is contracted and additional focusing thus takes place.

The ions are deflected from the direction of flow in the direction of the electrodes by the electric field, which develops between the electrodes 9, 10, 11, 12 arranged opposite each other. The auxiliary electrodes 10, 12 as well as the detector electrode 9 are on a lower potential than the counterelectrode 11 (positive mode) for the detection of positive ions. The auxiliary electrodes 10, 12 and the detector electrode 9 are ideally in one plane and at the same potential. Positive ions are thus deflected in the direction of the auxiliary electrodes 10, 12 and the detector electrode 9. In case of a corresponding deflecting voltage, only ions of a defined mobility will reach the detector electrode 9, because the velocity of flow and the velocity of deflection are at the correct ratio for these ions only. There is an ionic current between the detector electrode 9 and the counterelectrode 11, which is correlated with the concentration of these ions and hence with the concentration of the corresponding analyte in the ambient air.

To guarantee the development of the most uniform field possible, the counterelectrode 11 is located, congruently in terms of area, in parallel opposite the auxiliary electrodes 10, 12 and the detector electrode 9, which are located in one plane. An ion spectrum can be recorded by changing the deflecting voltage. Because of the ion focusing and the spectral analysis, the system has improved separation efficiency compared to other systems (e.g., ChemoPro 100 from the firm of Environics). The potential ratios can be reversed without problems (negative mode) for the detection of negatively charged ions. Switchover between the positive mode and negative mode is possible in the range of 1 to 5 Hz because of the low deflecting voltages.

The drift gas 5 is sent through a filter 13 after passing through the separation area 8 and is re-introduced into the transition area 3. As a result, moisture, analytes and other impurities are removed from the drift gas, i.e., the ion separation takes place in dry and clean air nearly independently from the ambient moisture.

Due to the reduction of the dimensions of the system, the amount of media needed is minimized. The simple design and the low manufacturing costs associated therewith are especially advantageous. The dynamic range of the system can be increased in a simple manner by changing the gas flows of both the ion carrier gas and the drift gas and by taking into account the changed flight distances by calculation.

Figure 2:
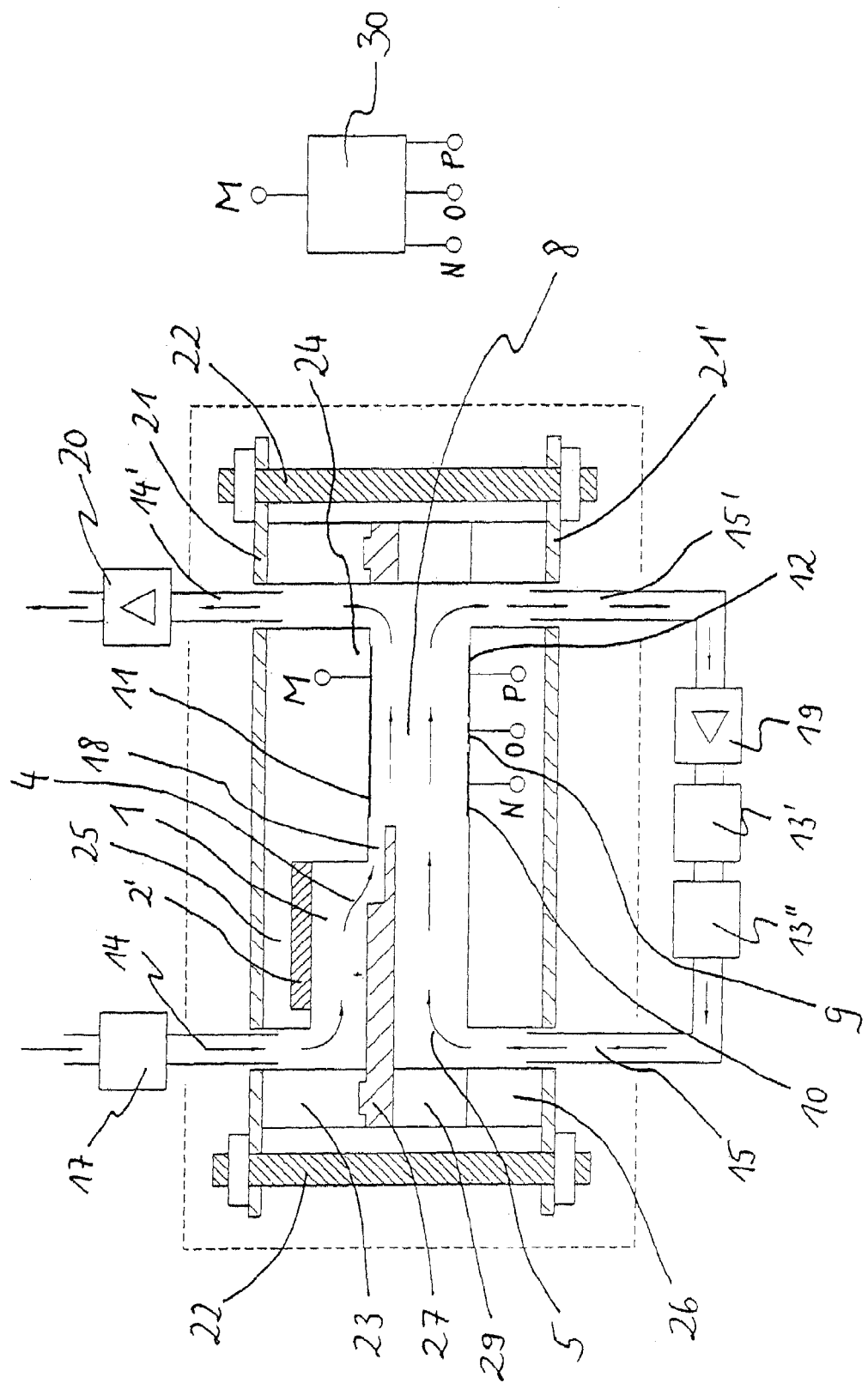
FIG. 2 is a schematic view of an especially assembly-friendly design of an ion mobility spectrometer according to the present invention in the form of a stacked array of formed parts.

FIG. 2 shows an especially assembly-friendly embodiment of an IMS according to the present invention. This is a stacked design comprising a plurality of formed parts, which are held in their positions between liming and tensioning means. The individual formed parts are shaped geometrically such that they ensure the division of space and flow guiding according to the present invention in the assembled state. A mount for a radiation source 2', gas connections 14, 15 for ion carrier gas 4 and drift gas 5, at least one auxiliary electrode 10 and a detector electrode 9 as well as a counterelectrode 11 are already integrated in the corresponding formed parts or attached to same.

The air to be analyzed is introduced via a particle filter 17 into the ionization chamber 1, where the analytes contained in the air are ionized. The ionization may be carried out by β-radiation (electrons) or UV radiation (photons). A radioactive tritium source 2' is used as the radiation source in the embodiment being described here. Air molecules are bombarded by the emitted β-radiation with high-energy electrons, as a result of which the nitrogen molecules in the air will at first be ionized. The analytes in the air are not directly ionized by the electron bombardment. Stable $H^+(H_2O)_n$ and $O_2^-$ $(H_2O)_n$ reactant ions as well as positive and negative analyte ions are formed in subsequent reactions. By crossing the ionization space 1, the air contains ions and represents an ion carrier gas 4 in the sense of the present invention.

The ion carrier gas 4 then flows through a slot-like narrowed section 18, as a result of which mechanical contraction or focusing of the ion carrier gas 4 takes place. Behind the slot-like narrowed section 18, the ion carrier gas 4 merges with the drift gas 5 in a laminar flow and a laminar flow of ion carrier gas 4 and drift gas 5 develops. Contrary to the preceding exemplary embodiment, a pronounced transition area is absent. However, this can be embodied without problems by a correspondingly stretched design of the individual formed parts.

Due to an electric field that extends at right angles to the direction of flow and develops between opposite electrodes, whose arrangement extensively corresponds to the preceding exemplary embodiment, the ions are deflected from the direction of flow in the direction of the electrodes. The auxiliary electrodes 10, 12 and the detector electrode 9 are on a lower potential than the counterelectrode 11 for the detection of positive ions. The auxiliary electrodes 10, 12 and the detector electrode 9 are on the same potential. Positive ions are deflected in the direction of the auxiliary electrodes 10, 12 and the detector electrode 9. In case of a corresponding deflecting voltage, only ions with a defined mobility will reach the detector electrode 9, because the ratio of the velocity of flow and the velocity of deflection is correct for this ion species only. An ionic current results between the detector electrode 9 and the counterelectrode 11, which is correlated with the concentration of these ions and hence with the concentration of the corresponding analyte in the ambient air.

An ion spectrum can be recorded by varying the deflecting voltage. Because of the focusing of the ions, which is brought about by fluidic engineering, and the spectral analysis, the system has improved separation efficiency compared to other systems. The potential ratios are transposed for the detection of the negative ions.

After flowing through the separation area 8, the drift gas 5 is pumped back into the system with a pump 19 through a molecular sieve 13' and an activated carbon filter 13". Moisture, analytes and other impurities are removed from the drift gas 5 as a result. Thus, the separation of the ions is carried out in dry, clean air, nearly independently from the ambient moisture. The ion carrier gas 4 is drawn with a pump 20 through the system and released into the environment.

Possible modifications of such an IMS can be embodied without problems due to the modular design by modifying individual formed parts. The individual formed parts (modules) are connected to one another in a gas-tight manner by being arranged as a stack between two steel plates 21, 21', which are braced against one another by screw connections 22, 22'.

An upper formed part 23 contains gas connections for the admission 14 and the discharge 14' of the ion carrier gas 4 as well as a mount for the radioactive tritium source 2'. The upper formed part 23 is provided with the counterelectrode 11 in an elevated area 24. This elevated area 24 forms at the same time a limitation of the separation area 8 in the mounted state of the IMS. The mount of the tritium source 2' is located in a set-back area 25 of the upper formed part 23, which area forms a limitation of the ionization space 1 in the mounted state.

A lower formed part 26 contains gas connections for the admission 15 and the discharge 15' of drift gas 5. Auxiliary electrodes 10, 12 and a detector electrode 9 are arranged on the lower formed part 26. The lower formed part 26 forms another limitation of the separation area 8. Because of the small dimensions, the electrodes are applied as a thin layer and are structured already during the deposition by means of a shadow mask or subsequently by photolithography.

Another formed part 27 between the upper and lower formed parts 23, 26 ensures the pneumatic uncoupling of the ionization space 1 and the separation area 8. This formed part 27 comprises a thin lip 28 and is mounted such that the lip 28 overlaps the elevated area 24 of the upper formed part 23. As a result, a slot-like narrowed section 18 is obtained, by which the focusing according to the present invention of the ion carrier gas 4 is brought about. The fact that the velocity of flow of the drift gas is higher than the velocity of flow of the ion carrier gas, an additional contraction of the ion carrier gas, which is advantageous for the further focusing of the ion carrier gas, takes place in the area of merging of the drift gas and the ion carrier gas.

Another formed part 29 is used as a spacer and defines the distance between the auxiliary electrodes 10, 12 and detector electrode 9, on the one hand, and the formed part 27, on the other hand. The electrode distance between the auxiliary electrodes 10, 12 and detector electrode 9, on the one hand, and the counterelectrode 11, on the other hand, is determined by the thicknesses of the formed parts 27 and 29.

PTFE (Teflon), Teflon-coated aluminum or a dimensionally stable, emission-free plastic is suitable for use as the material for the formed parts 23, 26 and 29. The electrodes are connected in all exemplary embodiments to a circuit 30, which ensures the potential distributions described. This circuit 30 is not shown in the following embodiments, but shall always be considered to be part of an IMS according to the present invention. Identical letters symbolize the connection of the inputs of the circuit with the individual electrodes.

Figure 3:
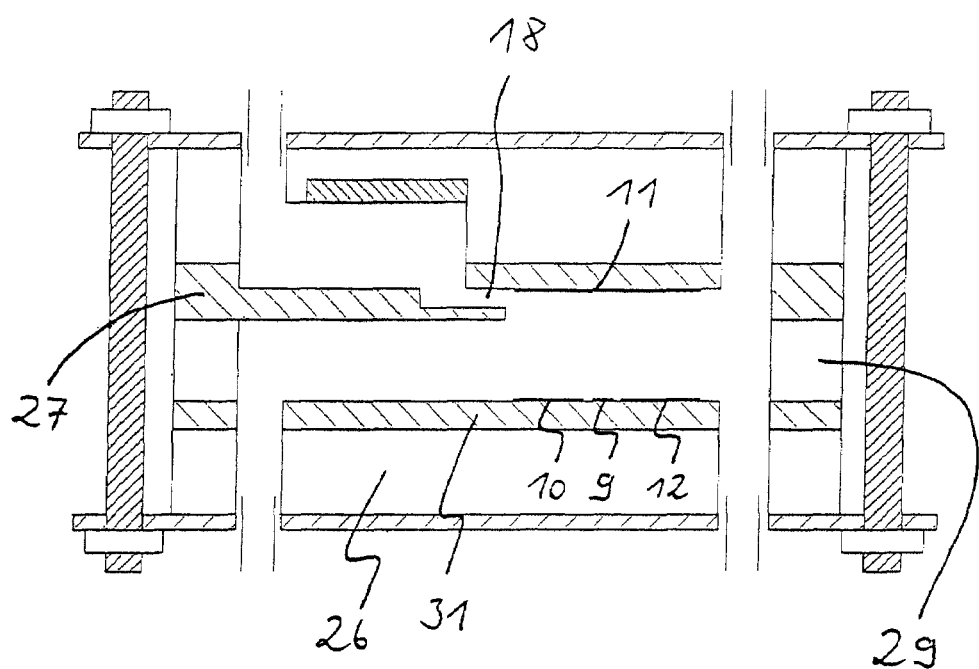
FIG. 3 is a slightly modified form of an IMS according to the present invention compared to FIG. 2.

FIG. 3. It may be technologically advantageous to arrange the auxiliary electrodes 10, 12 and the detector electrode 9 on a separate formed part 31, which is included in the stacked array according to the present invention between the lower formed part 26 and the formed part 29 acting as a spacer.

The embodiment of the slot-like narrowed section 18, through which the ion carrier gas 4 flows into the separation area 8, is of particular significance in the stacked array according to the present invention. It is therefore advantageous to manufacture the formed part 27 for the pneumatic uncoupling of the ionization space 1 and the separation area 8 with an already preset slot geometry. In this case, the formed part 27 contains the slot-like narrowed section 18 necessary for focusing the ion carrier gas 4 and the counterelectrode 11. The formed part 27 completely covers the upper formed part 23 in the direction of the separation area 8. The small dimensions of the slot-like narrowed section 18 require high-precision manufacture of the formed part 27. Manufacturing methods of the Microsystems technology are especially suitable here.

Figure 4:
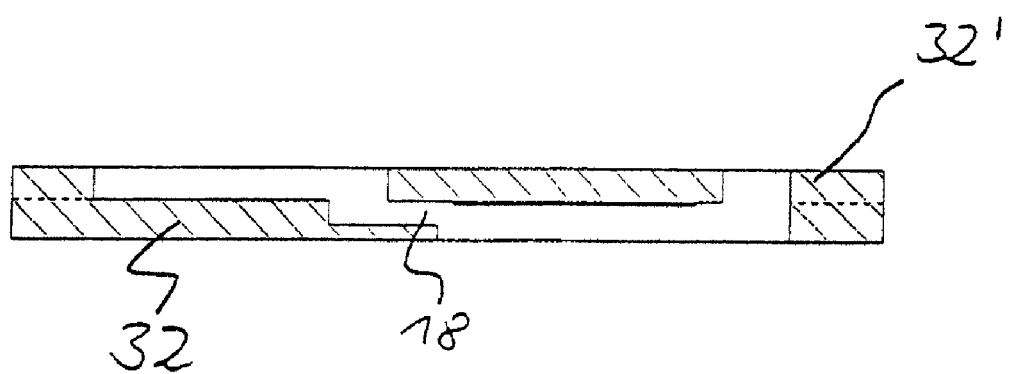
FIG. 4 is a sectional view of a formed part for the pneumatic uncoupling of the ionization space and the separation area with fixed slot geometry during manufacture.
Figure 5:
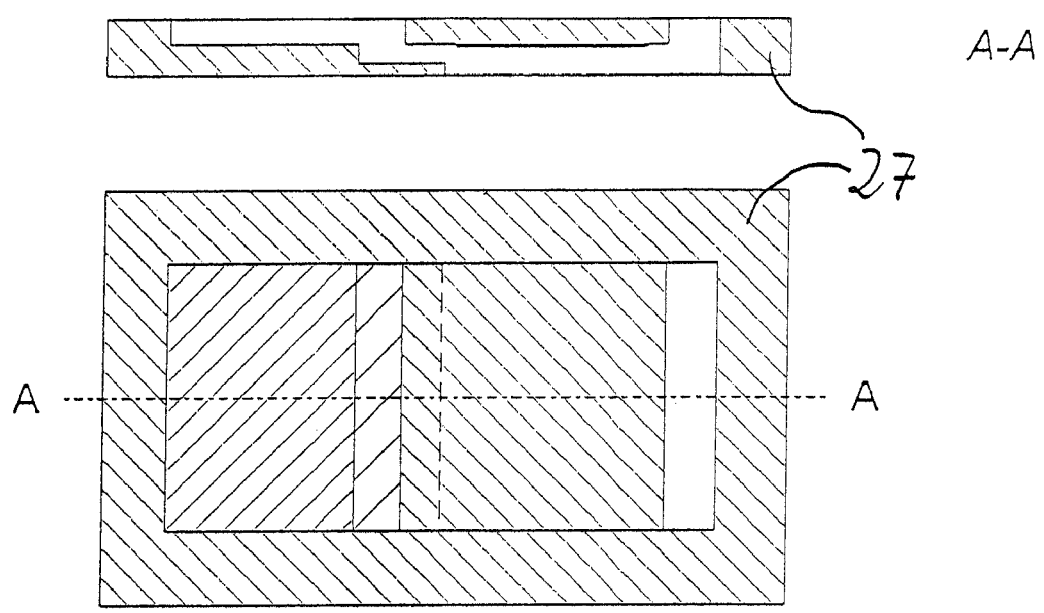
FIG. 5 is a sectional view and a top view of the same formed part for the pneumatic uncoupling of the ionization space and the separation area.

FIG. 4. An exactly defined narrowed section can be embodied by means of two formed parts 32 and 32', which are structured separately. The needed slot-like narrowed section 18 is formed by the lip 28 on the formed part 32 overlapping with the upper formed part 32'. Because of the necessary accuracy in the adjustment, during which the individual components 32, 32' may be displaced along the broken lines, the formed parts 32 and 32' are irreversibly connected to one another after the structuring, as a result of which the geometry of the slot cannot change any longer during the further assembly of the ion mobility spectrometer. A uniform formed part 27 for the pneumatic uncoupling of the ionization space and the separation area, which makes possible the flow conditions according to the present invention, is obtained according to FIG. 5.

Figure 6:
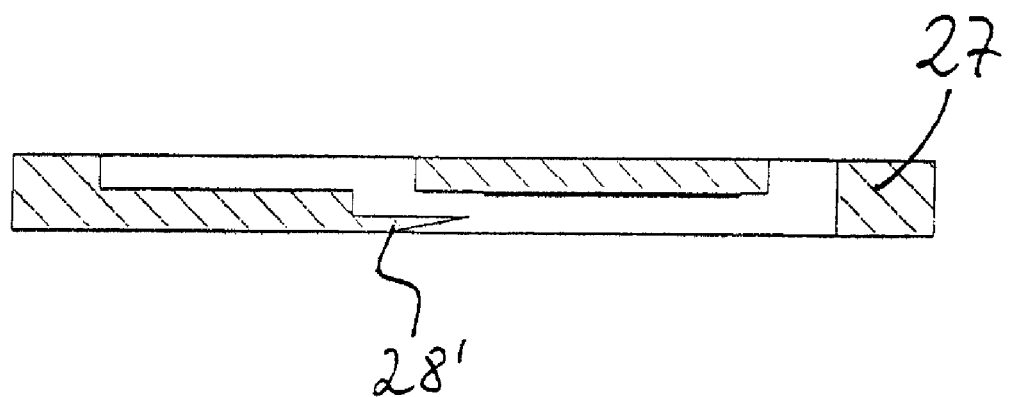
FIG. 6 is a sectional view of an alternative formed part for the pneumatic uncoupling of the ionization and the separation area with fixed slot geometry.

FIG. 6 shows a sectional view of an alternative formed part 27' for the pneumatic uncoupling of the ionization space 1 and the separation area 8 with fixed slot geometry. The lip 28' on the formed part 27' ideally tapers in the direction of flow, and its flanks converge at an acute angle. It is especially advantageous if only the side of the lip 28' facing the drift gas flow has a bevel.

Dimensionally stable, emission-free plastics, glass or Teflon-coated aluminum are also suitable materials for the formed parts 27 and 31.

Figure 7:
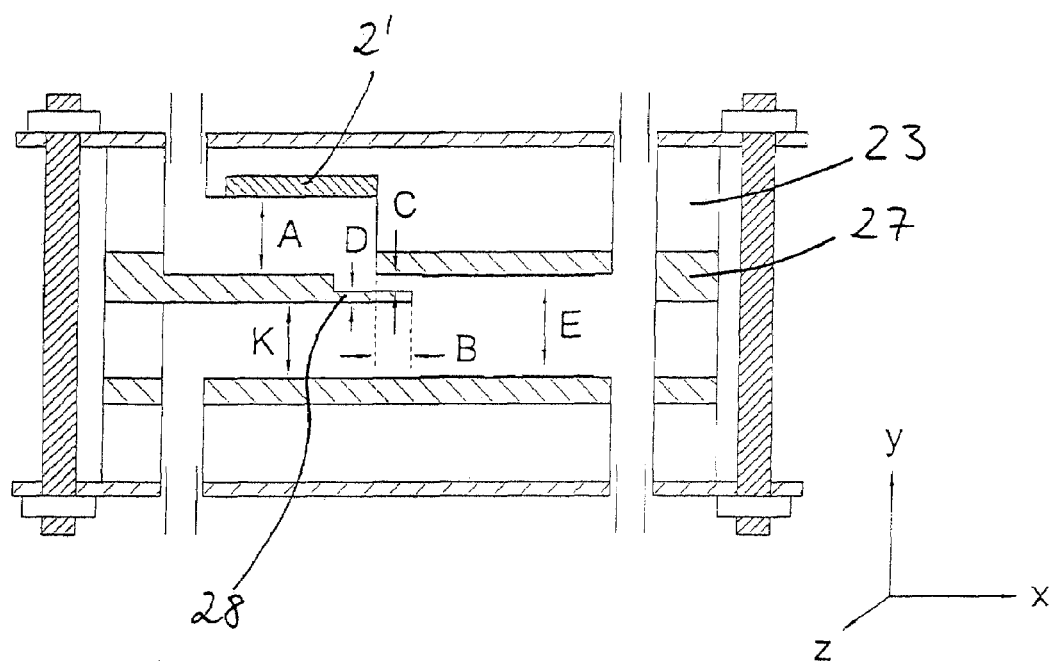
FIG. 7 is an ion mobility spectrometer in the form of a stacked array of formed parts with indication of dimensions that are essential for the function.

FIG. 7 shows an ion mobility spectrometer in the form of a stacked array of formed parts with the indication of dimensions that are relevant for the function, which will be explained in greater detail below. The ionization space 1 with a height A is formed by fitting together the formed parts 23 and 27. The optimal height A for a maximum ionic current is obtained from the velocity of flow and the residence time of the ions in the ionization area as well as the energy distribution of the radioactive source. The maximum depth of penetration of the radiation in air is 2 mm in the case of the tritium source 2' being used here, so that the height of the ionization space 1 should be 2 mm. To reduce the residence time of the ions in the ionization space 1 and thus to minimize ion losses due to wall reactions and recombination, a height smaller than 2 mm may be advantageous. In addition, the slot length B should be small. However, B should be at least 0.5 times the slot height C for fluidic reasons. To prevent vortices in the area of merging, the thickness D of the lip 28 should likewise be minimal. Therefore, the flanks of the lip 28 ideally converge at an acute angle.

For high resolutions, the height K of the drift gas inlet should be at least 20 times the slot height C if the velocities of admission of the ion carrier gas and the drift gas are equal. In principle, it can be stated that the higher the ratio of the velocity of flow of the drift gas to the velocity of flow of the ion carrier gas in the area of the merging, the stronger is the effect of focusing of the ion carrier gas behind the slot-like narrowed section. By selecting pumps 19, 20 with a corresponding capacity, it can be advantageously achieved that the velocity of flow of the drift gas 5 is even higher than the velocity of flow of the ion carrier gas 4 by a factor of at least 1.5.

Figure 8:
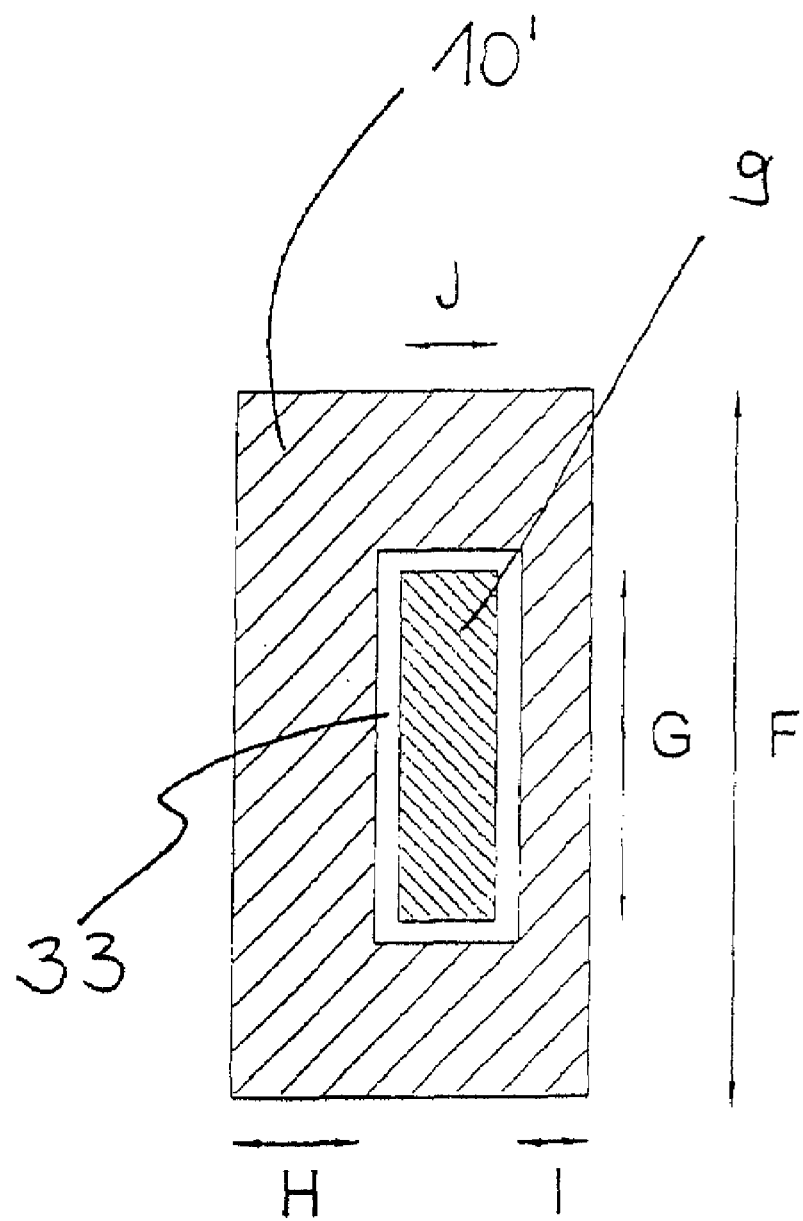
FIG. 8 is an advantageous electrode geometry with characteristic dimensions.

FIG. 8 shows an advantageous electrode geometry with characteristic dimensions. The dimensions and the positions of the auxiliary electrode 10' and the detector electrode 9 appear from the image of the slot height C into the electrode plane, taking into account the diffusion, the deflecting voltage and the velocity of flow in the separation area 8. The flight time of the ions should be minimized for minimal diffusion effects, i.e., the deflection from the direction of flow takes place ideally immediately behind the slot-like narrowed section 18 after the formation of the laminar flow. For the same reason, the height E of the separation area 8 and the width H of the auxiliary electrode 10' should be small. On the whole, the resolution can be further improved with progressing miniaturization. The disadvantageous effect of diffusion decreases due to the shortened flight times, but the relations that determine the function must be preserved.

Figure 9:
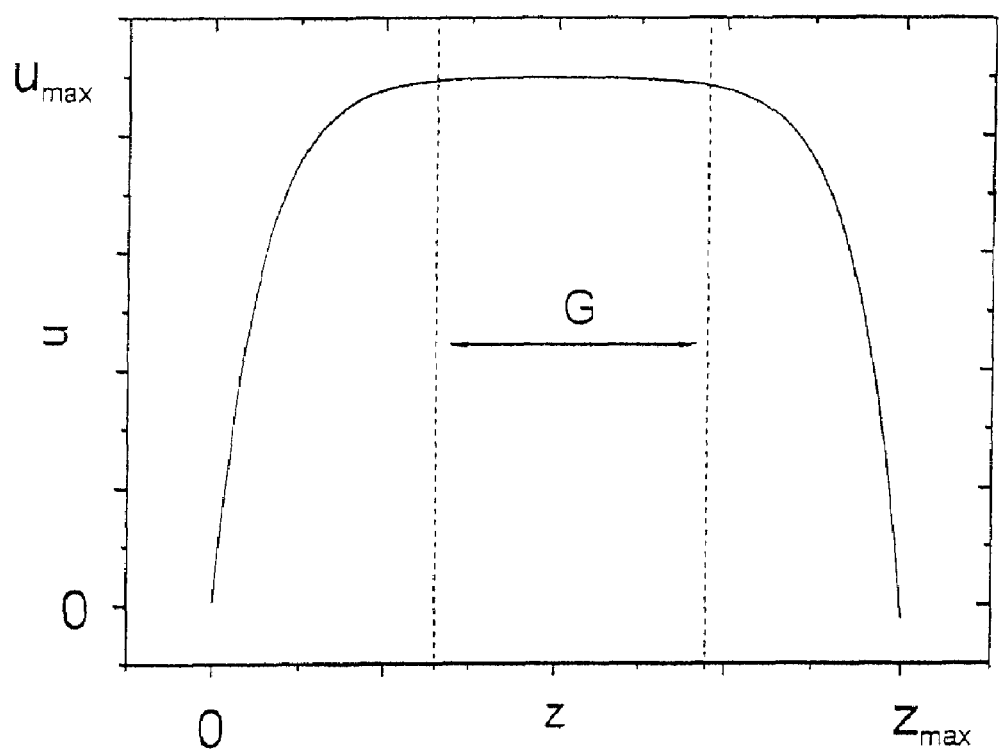
FIG. 9 is a flow profile in the inlet area of the separation area.

The ratio of the depth of the separation area F (in the z direction) to the height E of the separation area should be greater than 5, so that a flow profile as shown in FIG. 9 will become established in the z direction with the area of nearly constant velocity, which area is typical for flows in gaps. At a ratio of 5, a nearly constant area of length G is formed in the center of the separation area, which accounts for about 40% of the depth F of the separation area. To blank out ions from the marginal areas with variable velocity of flow, the detector electrode should correspond at most to the length G in the z direction and, as is shown in FIG. 8, should be positioned in the center of the separation area. The higher the ratio of the depth F of the separation area to the height E of the separation area becomes, the greater will be the length G, so that more and more ions will reach the detector electrode, and the ionic current will thus increase. To guarantee a uniform electric field, the auxiliary electrode 10' should completely surround the detector electrode, and the electrode distance 33 should be kept as narrow as possible. It proved to be advantageous if the distance 33 between the detector electrode 9 and the auxiliary electrode 10' surrounding same corresponds at most to 20% of the extension J of the detector electrode in the direction of flow.

Figure 10:
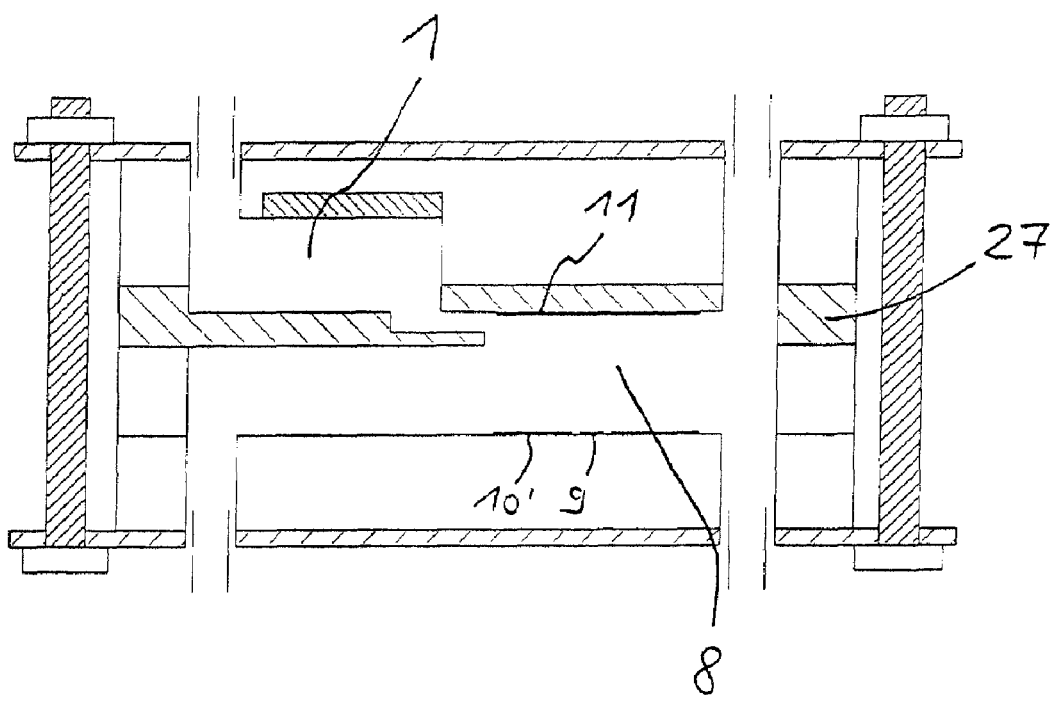
FIG. 10 is a slightly modified form compared to FIG. 2 of an IMS according to the present invention, in which the counterelectrode is part of a formed part for the pneumatic uncoupling of the ionization and the separation area.

Another embodiment of a stacked array according to the present invention is shown in FIG. 10. The counterelectrode 11 is deposited here as a thin layer on the formed part 27 for the pneumatic uncoupling of the ionization space 1 and the separation area 8. The auxiliary electrode 10' and the detector electrode 9 are, however, applied directly to the lower formed part 26.

Figure 11:
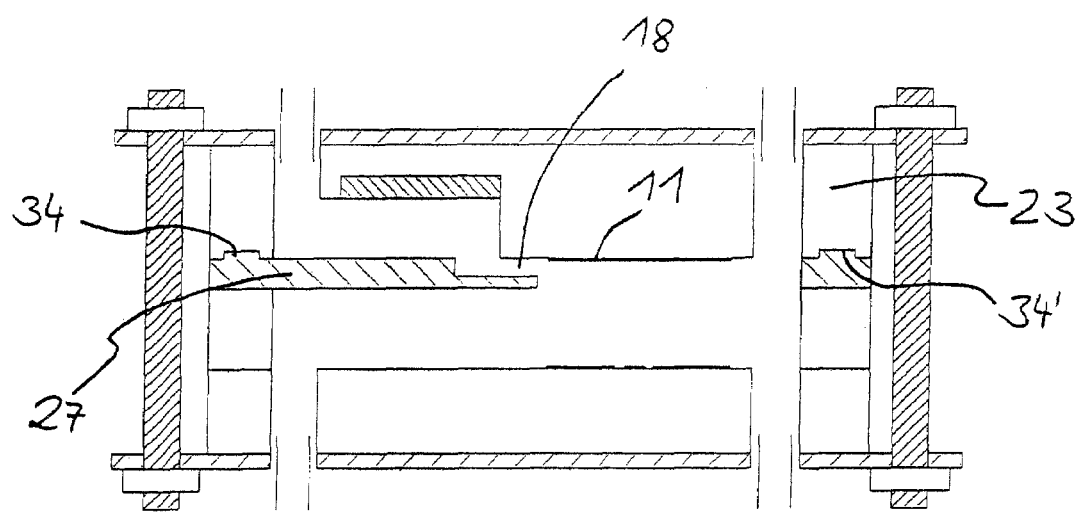
FIG. 11 is a slightly modified form compared to FIG. 2 of an IMS according to the present invention with self-adjusting armatures.

Another embodiment of a stacked array according to the present invention is shown in FIG. 11. The counterelectrode 11 is applied here as a thin layer directly to the upper formed part 23. The slot-like narrowed section 18 is formed due to the overlap of the formed parts 23 and 27. The slot height C is defined by the depression in the formed part 27. Accurate adjustment of the formed parts 23 and 27 is necessary in this embodiment to guarantee a defined geometry of the slot-like narrowed section 18. The formed parts are provided for this reason with high-precision self-adjusting armatures 34, 34', which ensure the corresponding alignment of the formed parts during the assembly of the ion mobility spectrometer.

Figure 12:
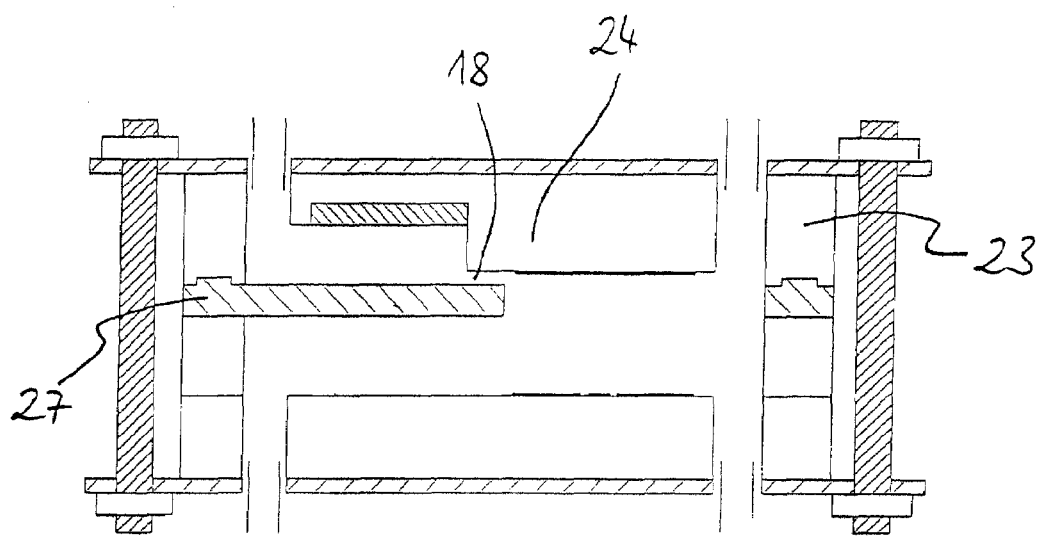
FIG. 12 is a slightly modified form compared to FIG. 11 of an IMS according to the present invention with self-adjusting armatures.

FIG. 12. In a slightly modified embodiment, the slot-like narrowed section 18 is embodied only by a reduced overall height of the elevated area 24 of the upper formed part 23 and an overlap with the formed part 27. The formed part 27 has only a large passage opening in this embodiment and can be structured in an especially simple manner. Aside from the clamping device, the system comprises in the embodiments shown only four formed parts, all of which can be manufactured in a simple manner.

Figure 13:
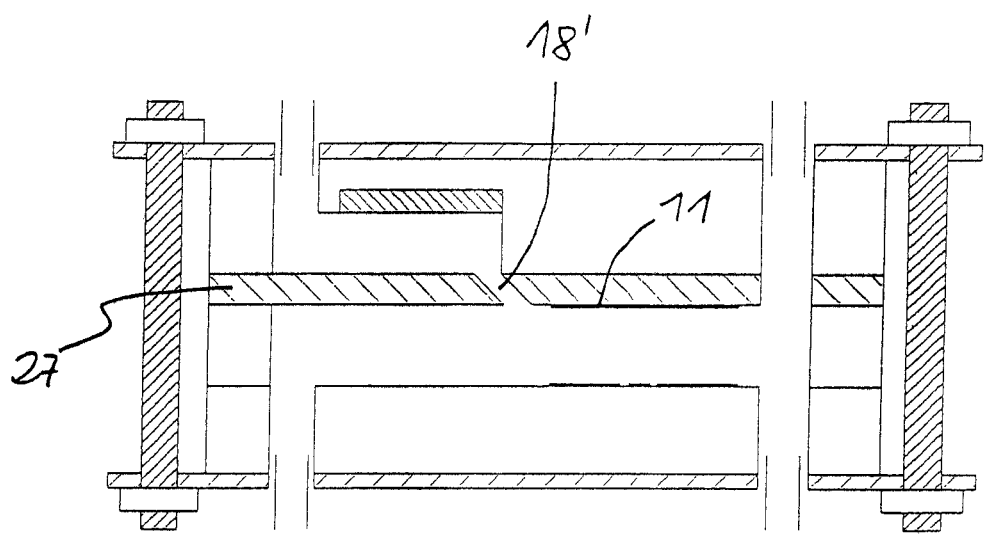
FIG. 13 is a slightly modified form compared to FIG. 2 of an IMS according to the present invention with an oblique slot for feeding the ion carrier gas.

FIG. 13. In another embodiment, the narrowed section 18' is integrated as an oblique slot in the formed part for the pneumatic uncoupling 27 of the ionization space and the separation area. The counterelectrode 11 is deposited as a thin layer on the formed part 27 and is structured by photolithography or by means of a shadow mask. The precision of the narrowed section 18' is determined by the manufacturing tolerances with which the formed part 27 is manufactured.

Figure 14:
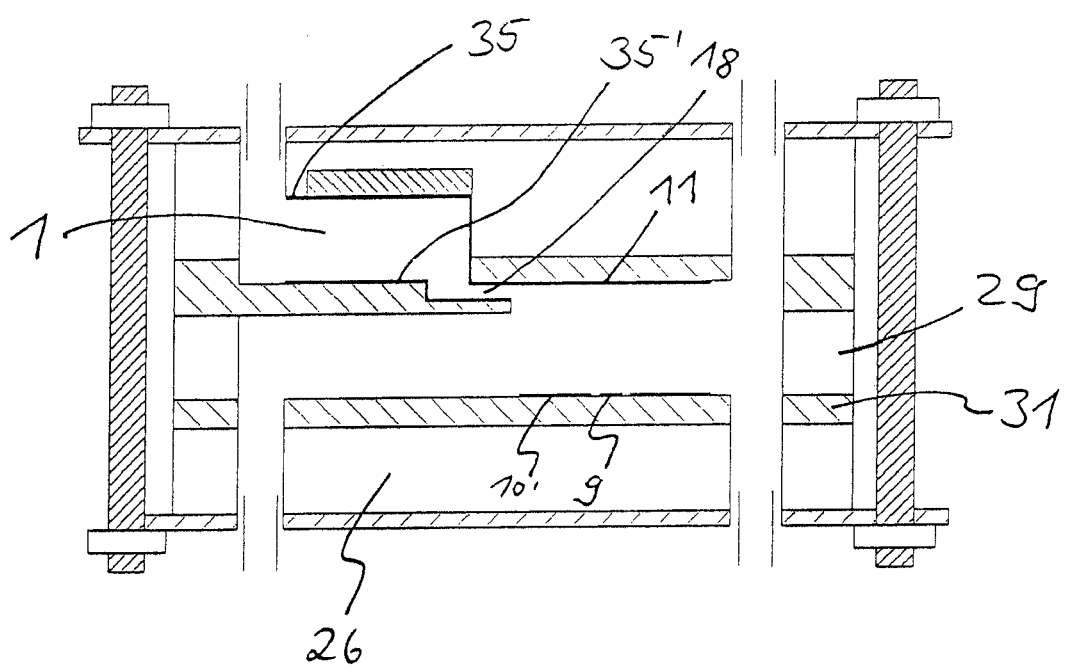
FIG. 14 is a slightly modified form compared to FIG. 2 of an IMS according to the present invention with a field-free design of the ionization space and with a slot-like narrowed section.

The ionization space 1 and the slot-like narrowed section 18 are surrounded in the embodiment shown in FIG. 14 by electrodes 35 and 35', which are at the same potential, so that the ions flow at first through a field-free area after they are formed before they are deflected in the separation area 8. The potentials of the electrodes 35 and 35' are ideally identical to the potential of the counterelectrode 11. Disturbing inhomogeneities of the electric field at the margin of the counterelectrode 11 in the area of the slot-like narrowed section 18 are thus eliminated. The electrodes 35 and 35' are coated with PTFE or another material having the same action in the ionization space 1 and the slot-like narrowed section 18 in order to minimize wall reactions. At the same time, it proved to be technologically advantageous to arrange the auxiliary electrode 10' and the detector electrode 9 on a separate formed part 31, which is inserted between the lower formed part 26 and the spacer 29.

A minimum amount of media is needed due to the reduction of the dimensions of the system. The simple design and the low manufacturing costs associated therewith are especially advantageous.

A resolution of about 15 can be obtained at flow rates of 1.5 L/minute for the drift gas and 75 mL/minute for the ion carrier gas with a narrowed section having a height C of 200 µm and a drift gas inlet height K of 4 mm as well as a separation area depth F of 20 mm. By reducing the slot height C to 20 µm, the height K to 400 µm and the depth F of the separation area to 10 mm, it is possible to reduce the flow rates to 150 mL/minute for the drift gas and to 7.5 mL/per minute for the ion carrier gas at equal resolution.

Figure 15:
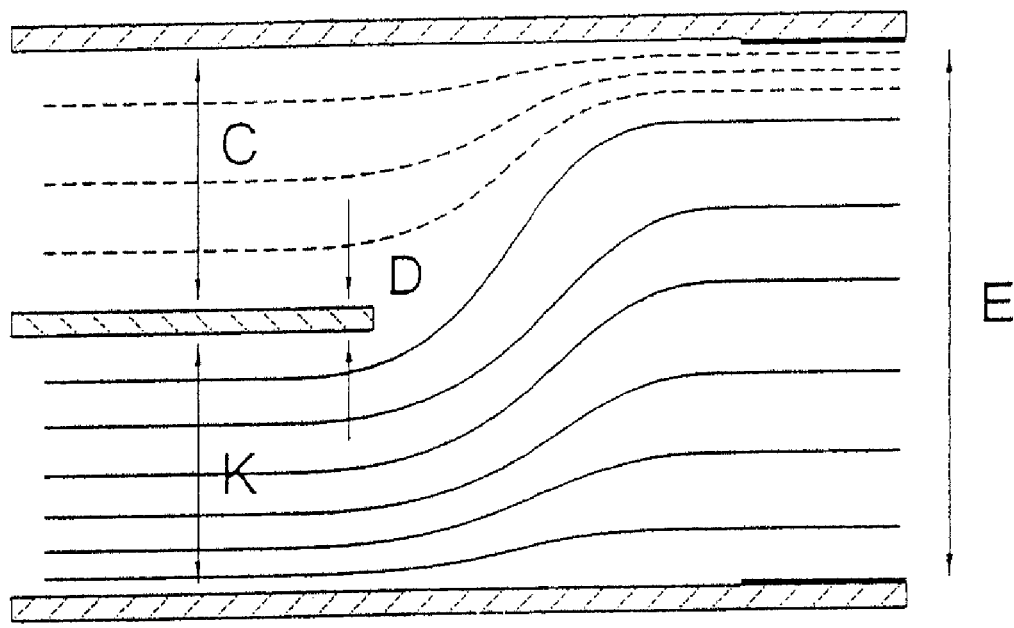
FIG. 15 is a view of the flow lines in an IMS according to the present invention in the area in which the two gas flows are fed in and the introduction thereof into the separation area.

FIG. 15 shows a flow pattern with the schematic course of the flow lines in an IMS according to the present invention in the area in which the two gas flows are fed in and are introduced into the separation area.

The drift gas is admitted at a higher flow rate than is the ion carrier gas. As a result, the flow of the ion carrier gas is contracted, which leads to focusing according to the present invention of the analyte ions in a narrow cross-sectional area. This effect can be advantageously combined with focusing by flow-carrying mechanical means or it can be used as the sole means for focusing.

Figure 16:
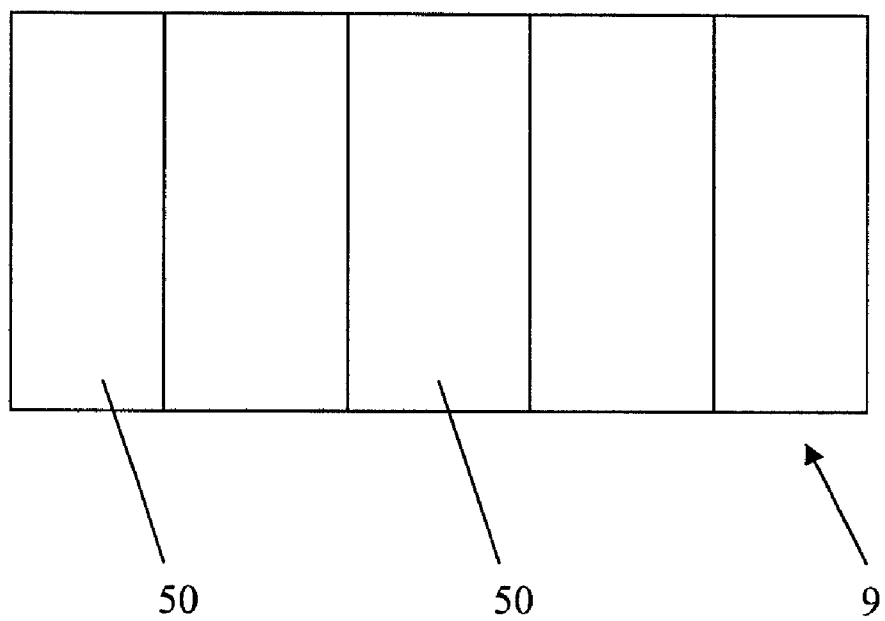
FIG. 16 is a bottom view of the detector.

FIG. 16 shows a bottom view of the detector 9, where the detector 9 has a plurality of sectors 50. The sectors 50 can be wired individually.

While specific embodiments of the invention have been shown and described in detail to illustrate the application of the principles of the invention, it will be understood that the invention may be embodied otherwise without departing from such principles.

What is claimed is:

1. An ion mobility spectrometer, comprising:
an ionization chamber, through which analyte-containing gas can flow;
a radiation source, from which ionizing radiation, which is suitable for at least partially ionizing the analyte-containing gas, enters said ionization chamber;
a separation area located behind said ionization space in the direction of flow, into which the partially ionized gas as an ion carrier gas and a nearly ion-free gas as a drift gas are introduced in such a way that a flow becomes established at least in an inlet area of said separation area, said flow comprising an ion carrier gas cross-sectional area through which predominantly said ion carrier gas flows and drift gas cross-sectional areas through which predominantly said drift gas flows, with said drift gas and said ion carrier gas flowing unidirectionally, said ion carrier gas cross-sectional area being smaller in at least one dimension than said drift gas cross-sectional areas;
a detector electrode;
an auxiliary electrode; and
a counterelectrode, said detector electrode, said auxiliary electrode and said counterelectrode being arranged in said separation area such that an electric field can develop between them, said electric field having at least one field component that is not parallel to the direction of flow in said separation area, at least one of said drift gas cross-sectional areas being located between said ion carrier gas cross-sectional area and said detector electrode.

2. An ion mobility spectrometer in accordance with claim 1, further comprising formed parts arranged in a stack-like manner including:
at least one formed part containing gas connections for said ion carrier gas;
at least one formed part containing gas connections for said drift gas;
at least one formed part containing a mount for a radiation source;
at least one formed part containing said auxiliary electrode and said detector electrode; and
at least one formed part containing said counterelectrode, and said formed parts cooperating in an assembled form and being shaped to define said ionization chamber, said separation area and a slot-like narrowed section for focusing said ion carrier gas.

3. An ion mobility spectrometer in accordance with claim 2, wherein said formed parts are arranged in said assembled form in a stack-like manner braced against one another in a gas-tight manner.

4. An ion mobility spectrometer in accordance with claim 2, wherein at least some of said formed parts consist essentially of Polytetrafluoroethylene-coated aluminum.

5. An ion mobility spectrometer in accordance with claim 2, wherein at least some of said formed parts consist essentially of emission-free, dimensionally stable plastics.

6. An ion mobility spectrometer in accordance with claim 2, wherein at least some of said formed parts consist essentially of glass.

7. An ion mobility spectrometer in accordance with claim 2, wherein at least some of said formed parts consist essentially of Polytetrafluoroethylene.

8. An ion mobility spectrometer in accordance with claim 2, wherein one of said formed parts has a fixed slot geometry for focusing said ion carrier gas and for the pneumatic uncoupling of said ionization chamber and said separation area.

9. An ion mobility spectrometer in accordance with claim 8, wherein said one of said formed parts with fixed slot geometry for focusing said ion carrier gas comprises two parts, which are connected to one another, wherein a slot-like narrowed section is formed by the overlapping of a projecting lip of one said parts with another of said parts.

10. An ion mobility spectrometer in accordance with claim 9, wherein a lip forming said slot-like narrowed section has flanks that converge at an acute angle and which is dimensionally stable.

11. An ion mobility spectrometer in accordance with claim 9, wherein a height (K) of a drift gas inlet corresponds to at least 10 times a height (C) of said slot-like narrowed section.

12. An ion mobility spectrometer in accordance with claim 11, wherein a ratio of a drift gas flow rate to an ion carrier gas flow rate corresponds at least to the ratio of K to C.

13. An ion mobility spectrometer in accordance with claim 9, wherein a length (B) of said slot-like narrowed section corresponds to at least half said slot height (C) of said slot-like narrowed section.

14. An ion mobility spectrometer in accordance with claim 9, wherein said radiation source is arranged such that an area in said ionization space, in which the ionization takes place, adjoins said slot-like narrowed section.

15. An ion mobility spectrometer in accordance with claims 9, wherein said ionization space and said slot-like narrowed section are surrounded at least partially by electrodes, which are on the same potential and generate a field-free area.

16. An ion mobility spectrometer in accordance with claim 2, wherein a drift gas flow rate in an area of a merging of said drift gas and said ion carrier gas is greater than an ion carrier gas flow rate by a factor of at least 1.5.

17. An ion mobility spectrometer in accordance with claim 2, wherein a depth (F) of said separation area corresponds at least to 5 times a height (E) of said separation area.

18. An ion mobility spectrometer in accordance with claim 2, wherein said detector electrode is positioned in a middle area of said separation area and is dimensioned corresponding to a length (G) of a nearly constant area of a flow profile in the a z direction.

19. An ion mobility spectrometer in accordance with claim 2, wherein said detector electrode is completely surrounded by an auxiliary electrode in one plane.

20. An ion mobility spectrometer in accordance with claim 1, further comprising a pump at an ion carrier gas outlet.

21. An ion mobility spectrometer in accordance with claim 1, further comprising a particle filter at an ion carrier gas inlet.

22. An ion mobility spectrometer in accordance with claim 1, wherein a distance between said detector electrode and said auxiliary electrode corresponds to at most 20% of a width (J) of said detector electrode in an x direction.

23. An ion mobility spectrometer in accordance with claim 1, wherein said ion carrier gas cross-sectional area is smaller in at least one dimension by a factor of at least 10 than said drift gas cross-sectional areas.

24. An ion mobility spectrometer in accordance with claim 1, further comprising an assembly unit connected to said separation area for maintaining a drift gas circuit.

25. An ion mobility spectrometer in accordance with claim 24, wherein said drift gas circuit contains a filter for at least one of reducing moisture, removing analytes and removing ions from said drift gas.

26. An ion mobility spectrometer in accordance with claim 25, further comprising:
a pump;
a molecular sieve; and
an activated carbon filter, said pump, said molecular sieve and said activated carbon filter being contained in said drift gas circuit.

27. An ion mobility spectrometer in accordance with claim 1, further comprising a radiation source for converting analyte-containing air admitted into said ionization space into said ion carrier gas by ionization of the air molecules in said ionization space, as a result of which the formation of analyte ions by subsequent reactions is made possible.

28. An ion mobility spectrometer in accordance with claim 1, further comprising a radiation source for converting analyte-containing air admitted into said ionization space into said ion carrier gas by direct ionization of said analyte molecules.

29. An ion mobility spectrometer in accordance with claim 28, wherein said radiation source includes an electron source comprising a beta radiator.

30. An ion mobility spectrometer in accordance with claim 1, further comprising flow-carrying means for focusing of said ion carrier gas.

31. An ion mobility spectrometer in accordance with claim 1, wherein surfaces that come into contact with said ion carrier gas consist of a material with low surface energy.

32. An ion mobility spectrometer in accordance with claim 1, wherein surfaces that come into contact with said ion carrier gas consist essentially of Polytetrafluoroethylene.

33. An ion mobility spectrometer in accordance with claim 1, further comprising: means for feeding said ion carrier gas and said drift gas such that said drift gas flows in at least 1.5 times faster than said ion carrier gas.

34. An ion mobility spectrometer in accordance with claim 1, further comprising: a circuit for maintaining said auxiliary electrode and said detector electrode at the same electric potential.

35. An ion mobility spectrometer in accordance with claim 1, wherein further comprising a circuit for producing a potential distribution at which a potential of said counterelectrode is higher than a potential of said detector electrode and a potential of said auxiliary electrode.

36. An ion mobility spectrometer in accordance with claim 1, further comprising: a circuit which produces a potential distribution at which the potential of said counterelectrode is lower than a potential of said detector electrode and a potential of said auxiliary electrode.

37. An ion mobility spectrometer in accordance with claim 1, further comprising: a circuit which produces a potential distribution at which a potential of said counterelectrode alternatingly becomes higher and lower than a potential of said detector electrode and a potential of said auxiliary electrode.

38. An ion mobility spectrometer in accordance with claim 1, further comprising: a circuit which produces a potential distribution at which the potential difference between said counterelectrode and at least said detector electrode varies.

39. An ion mobility spectrometer in accordance with claim 38, wherein said circuit produces a potential distribution at which the potential difference between said counterelectrode and said detector electrode jumps between a plurality of fixed values.

40. An ion mobility spectrometer in accordance with claim 1, further comprising another auxiliary electrode wherein at least one said auxiliary electrode is located in front of said detector electrode when viewed in the direction of flow.

41. An ion mobility spectrometer in accordance with claim 40, wherein at least one said auxiliary electrode is located behind said detector electrode when viewed in the direction of flow.

42. An ion mobility spectrometer in accordance with claim 1, wherein said counterelectrode, said auxiliary electrode and said detector electrode are arranged such that the electric field develops at right angles to the direction of flow.

43. An ion mobility spectrometer in accordance with claim 1, wherein said detector electrode is comprised of an individual electrode.

44. An ion mobility spectrometer in accordance with claim 1, wherein said detector electrode comprises a plurality of sectors that can be wired individually.

45. An ion mobility spectrometer in accordance with claim 1, wherein said counterelectrode, said auxiliary electrode and said detector electrode are arranged in parallel to one another.

46. An ion mobility spectrometer in accordance with claim 1, further comprising another auxiliary electrode wherein said auxiliary electrodes and said detector electrode are arranged in one plane.

47. An ion mobility spectrometer in accordance with claim 1, wherein said counterelectrode is arranged in one area, said detector electrode and said auxiliary electrode are arranged in another area, and a surface area of said one area and a surface area of said another area have the same size.

48. An ion mobility spectrometer in accordance with claim 47, wherein said one area in which said counterelectrode is arranged and said another area in which said detector electrode and said auxiliary electrodes are arranged are located congruently opposite each other.

49. An ion mobility spectrometer in accordance with claim 1, wherein said counterelectrode, said auxiliary electrode and said detector electrode consist of platinum or gold.

50. An ion mobility spectrometer in accordance with claim 1, wherein said detector electrode is narrower at right angles to the direction of flow than said cross-sectional area in said inlet area of said separation area, through which predominantly said ion carrier gas flows.

51. An ion mobility spectrometer in accordance with claim 1, wherein said flow is variable.

* * * * *

UNITED STATES PATENT AND TRADEMARK OFFICE
CERTIFICATE OF CORRECTION

PATENT NO. : 7,417,224 B2  Page 1 of 1
APPLICATION NO. : 11/420116
DATED : August 26, 2008
INVENTOR(S) : Zimmermann et al.

It is certified that error appears in the above-identified patent and that said Letters Patent is hereby corrected as shown below:

On the title page, item [73] should read:

Assignee: Dräger Safety AG & Co. KGaA
Lübeck (DE)

Signed and Sealed this

Twenty-eighth Day of October, 2008

JON W. DUDAS
*Director of the United States Patent and Trademark Office*